United States Patent [19]

Lipschutz

[11] Patent Number: 5,469,851
[45] Date of Patent: Nov. 28, 1995

[54] TIME MULTIPLEXED DIGITAL ULTRASOUND BEAMFORMER

[75] Inventor: David Lipschutz, Lexington, Mass.

[73] Assignee: Hewlett-Packard Company, Palo Alto, Calif.

[21] Appl. No.: 287,689

[22] Filed: Aug. 9, 1994

[51] Int. Cl.[6] .............................. A61B 8/00; G01N 29/00
[52] U.S. Cl. ...................................... 128/661.01; 73/626
[58] Field of Search ..................................... 367/103, 105; 128/660.07, 661.01; 73/625–626

[56] References Cited

U.S. PATENT DOCUMENTS

| | | | |
|---|---|---|---|
| 3,787,852 | 1/1974 | Puckette et al. | 343/7.7 |
| 4,001,763 | 1/1977 | Kits van Heyningen | 340/3 PS |
| 4,107,685 | 8/1978 | Martin et al. | 343/100 SA |
| 4,159,462 | 6/1979 | Rocha et al. | 340/1 R |
| 4,170,766 | 10/1979 | Pridham et al. | 367/135 |
| 4,173,007 | 10/1979 | McKeighen et al. | 367/11 |
| 4,213,195 | 7/1980 | Pridham | 367/92 |
| 4,252,026 | 2/1981 | Robinson | 73/626 |
| 4,267,584 | 5/1981 | McKeighen et al. | 367/11 |
| 4,274,148 | 6/1981 | van't Hullenaar | 367/122 |
| 4,275,461 | 6/1981 | Sternick et al. | 367/122 |
| 4,290,127 | 9/1981 | Pridham et al. | 367/123 |
| 4,290,310 | 9/1981 | Anderson | 73/626 |
| 4,401,957 | 8/1983 | McKeighen et al. | 333/165 |
| 4,604,736 | 8/1986 | Demeure | 367/123 |
| 4,622,634 | 11/1986 | Fidel | 364/414 |
| 4,644,795 | 2/1987 | Augustine | 73/625 |
| 4,750,367 | 6/1988 | Bernatets | 128/660.07 |
| 4,790,320 | 12/1988 | Perten et al. | 128/661.01 |
| 4,804,963 | 2/1989 | Clapham | 342/195 |
| 4,841,491 | 6/1989 | Kondo et al. | 367/103 |
| 4,886,069 | 12/1989 | O'Donnell | 128/661.01 |
| 4,893,283 | 1/1990 | Pesque | 367/138 |
| 5,005,419 | 4/1991 | O'Donnell et al. | 73/626 |
| 5,027,821 | 7/1991 | Hirama et al. | 128/661.01 |
| 5,121,361 | 6/1992 | Harrison, Jr. et al. | 367/135 |
| 5,228,007 | 7/1993 | Murakami et al. | 367/103 |
| 5,345,426 | 9/1994 | Lipschutz | 128/661.01 |

OTHER PUBLICATIONS

T. K. Song et al., "A New Dig. Phased Array Sys. for Dynamic Focusing & Steering with Reduced Sampling Rate", Ultrasonic Imaging 12, 1–16, 1990.

R. E. McKeighen et al., "New Tech. for Dynamically Var. Elect. Delays for Real Time Ultra. Imaging", 1977 Ultra. Symp. Proc. IEEE Cat. #77CH1264–ISU, p. 250.

R. G. Pridham et al., "Digital Interpolation Beamforming for Low–Pass & Bandpass Signals", IEEE Proceedings, vol. 67, No. 6, Jun. 1979, pp. 909–914.

Primary Examiner—Francis Jaworski

[57] ABSTRACT

A phased array digital ultrasound beamformer for use with an ultrasound transducer array. The beamformer includes a processing channel for each element of the transducer array. Each processing channel includes a digitizing circuit for converting the received signal to digital samples and a time multiplexed digital delay circuit responsive to delay coefficients for delaying the digital samples by time multiplexed delays to produce delayed, time multiplexed samples for forming two or more receive beams. The ultrasound beamformer further includes a summing circuit for summing the delayed, time multiplexed digital samples from each processing channel to form a stream of time multiplexed output samples that is simultaneously representative of two or more receive beams. A coefficient generator supplies the delay coefficients to the time multiplexed delay circuit in each of the processing channels.

22 Claims, 11 Drawing Sheets

TIME MULTIPLEXED DIGITAL ULTRASOUND BEAMFORMER

FIELD OF THE INVENTION

This invention relates to ultrasound imaging systems which utilize phased array beam steering and focusing and, more particularly, to a receive beamformer that processes two or more received beams simultaneously using time multiplexing.

BACKGROUND OF THE INVENTION

In a phased array ultrasound imaging system, the ultrasound transducer includes an array of transducer elements. The system includes n parallel channels, each having a transmitter and a receiver connected to one of the transducer array elements. Each transmitter outputs an ultrasound pulse through the transducer element into an object being imaged, typically the human body. The transmitted ultrasound energy is steered and focused by applying appropriate delays to the pulses transmitted from each array element so that the transmitted energy adds constructively at a desired point. The pulse is partially reflected back to the transducer array by various structures and tissues in The body.

Steering and focusing of the received ultrasound energy is effected in a reverse manner. The reflected ultrasound energy from an object or structure arrives at the array elements at different times. The received signals are amplified, delayed and then summed in a receive beamformer. The delay for each element is selected such that the received beam is focused at a desired point. The delays may be varied dynamically so as to focus the beam at progressively increasing depths, or ranges, as the ultrasound energy is received. The transmitted beam is scanned over a region of the body, and the signals generated by the beamformer are processed to produce an image of the region.

One important consideration in ultrasound imaging is the image sequence rate, or frame rate. The frame rate is limited by the speed of propagation of the ultrasound energy in the human body, the depth being examined and the number of scan lines used to form the image. The frame rate is particularly critical for color Doppler imaging of blood flow and for producing high resolution images.

One approach to increasing the frame rate is to receive beams from more than one direction at the same time within the spread of the transmitted pattern. In another high frame rate approach, several widely spaced receive beams are processed at the same time. A third class of applications for multiple receive beams involves using a "normal" transmit pattern and many receive beams in order to approximately calculate a complete synthetic aperture data set, from which several useful image enhancements can be calculated. In prior art systems, multiple receive beams are formed by multiple beamformers operating in parallel. However, because of the large amount of circuitry required for each beamformer, this approach is very expensive and impractical.

U.S. Pat. No. 4,644,795, issued Feb. 24, 1987 to Augustine, discloses a multiline ultrasonic beamformer which utilizes a $\sin(\pi x)/\pi x$ transmit excitation, and the received signals are applied to parallel delay paths.

U.S. Pat. No. 4,790,320, issued Dec. 13, 1988 to Perten et al discloses an ultrasound imaging system wherein delay processors, such as dual port RAMS, include incremental delays in order to perform parallel beamforming simultaneously.

U.S. Pat. No. 4,886,069, issued Dec. 12, 1989 to O'Donnell, discloses a technique for obtaining return signals from M different beam directions simultaneously by demodulating return signals and rotating the phases of the received signals.

U.S. Pat. No. 4,622,634, issued Nov. 11, 1986 to Fidel, discloses a system for parallel processing of ultrasound vectors wherein first and second memories are alternately loaded with vector information. The vector information is read out from the memories at different times.

U.S. Pat. No. 4,893,283, issued Jan. 9, 1990 to Pesque, discloses an ultrasound system wherein the transmitter transmits M beams sequentially during a very short time period, and the receiver simultaneously receives the echoes of the M beams.

U.S. Pat. No. 5,121,361, issued Jun. 9, 1992 to Harrison, Jr. et al, discloses a programmable beamformer including first and second programmable beam focusing modules which operate alternately to focus in different zones. It appears that only one beam is formed.

U.S. Pat. No. 4,252,026, issued Feb. 24, 1981 to Robinson, discloses an ultrasonic system wherein a plurality of beamforming circuits provide receive beams for each pulse transmitted.

U.S. Pat. No. 4,173,007, issued Oct. 30, 1979 to McKeighen et al, discloses an ultrasound imaging system using a memory with separate read and write capabilities to produce a dynamically variable delay. The delay can be varied by modifying the write or the read address pointer.

SUMMARY OF THE INVENTION

In accordance with the present invention, an ultrasound beamformer for processing received signals from an ultrasound transducer array comprises a plurality of processing channels, each receiving a signal from an element of the transducer array. Each processing channel comprises digitizing means for converting the received signal to digital samples at a sampling rate f, and time multiplexed delay means responsive to delay coefficients for delaying the digital samples by time multiplexed delays to produce delayed, time multiplexed samples for forming two or more receive beams. The ultrasound beamformer further comprises summing means for summing the delayed, time multiplexed digital samples to form a stream of time multiplexed output samples that is representative of the two or more receive beams, and a coefficient generator for supplying the delay coefficients to the time multiplexed delay means in each of the processing channels.

Preferably, the time multiplexed delay means comprises delay means for delaying the digital samples by selected delays that are quantized in increments equal to the sampling period 1/f. The delay means preferably comprises memory means for snoring the digital samples, means for writing the digital samples into the memory means and time multiplexed read means for reading digital samples from the memory means at locations corresponding to the time multiplexed delays. In a first embodiment, the memory means comprises a two-port random access memory. The read means can comprise a read counter for each receive beam being processed and multiplexer means for applying the output of a selected read counter to the memory means in response to an interleave control signal representative of a receive beam being processed during each clock cycle. The read counter preferably includes means for addressing a location in the memory means corresponding to a desired delay. Preferably, the time multiplexed delay means further includes a focal delay generator corresponding to each read counter. Each focal delay generator controls the state of the corresponding read counter in response to the delay coefficients.

In another feature of the invention, the time multiplexed delay means may further include primary and neighbor beam delay processing means for processing the delayed digital samples output by the integer clock delay means to provide a first data stream containing time multiplexed digital samples for forming two or more primary beams and a second data stream containing time multiplexed digital samples for forming two or more neighbor beams. Each neighbor beam has a corresponding primary beam and each neighbor beam is within a predetermined range of angles of the corresponding primary beam. The primary and neighbor beam delay processing means preferably comprises primary beam delay means for applying a fixed additional delay to the delayed digital samples to provide the first data stream, and neighbor beam delay means for removing the delays previously applied to the delayed digital samples and applying neighbor beam delays that are within a predetermined number of clock cycles of the primary beam delays to provide the second data stream.

In a second embodiment, the memory means comprises a three-port random access memory having a write port, a first read port and a second read port. The time multiplexed read means comprises a first read address control for supplying first interleaved addresses to the first read port and a second read address control for supplying second interleaved addresses to the second read port. The first read port supplies a first stream of time multiplexed data samples in response to the first interleaved addresses, and the second read port supplies a second stream of time multiplexed data samples in response to the second interleaved addresses. The three port random access memory provides two groups of time multiplexed receive beams without requiring the primary and neighbor beam delay processing circuitry described above. The two groups of receive beams are not required to be within a prescribed angular offset from each other, as in the case of the primary and neighbor beams. Preferably, the time multiplexed delay means further comprises a delay interpolator for delaying the digital samples by selected subdelays that are quantized in increments less than the sampling period 1/f. The delay interpolator preferably comprises an FIR digital filter having programmable means responsive to filter coefficients for delaying the digital samples by different subdelays that are quantized in increments less than the sampling period 1/f, means for supplying the filter coefficients to the FIR digital filter in response to a subdelay control signal, means for generating the subdelay control signal in response to the delay coefficients and means for storing groups of consecutive digital samples representative of each receive beam for time multiplexed application to the FIR digital filter during different clock cycles.

The digitizing means preferably comprises an amplifier for amplifying the received signal, a limiter for limiting the amplified signal, a low pass filter for removing high frequency components from the limited signal and an analog-to-digital converter for converting the limited and filtered signal to digital samples. The limiter preferably includes means for preventing the analog-to-digital converter from saturating. The low pass filter has a cutoff frequency corresponding to the sampling rate f.

The summing means preferably has a pipeline structure and includes summing the delayed digital samples for a plurality of groups of processing channels to provide a plurality of intermediate sums during a first clock cycle and means for summing the plurality of intermediate sums during a second clock cycle to form a sum representative of the plurality of groups of processing channels. The summing means preferably further includes programmable means for adding different pipeline delays to the output of the summing means in response to an interleave factor representative of the number of receive beams being processed.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
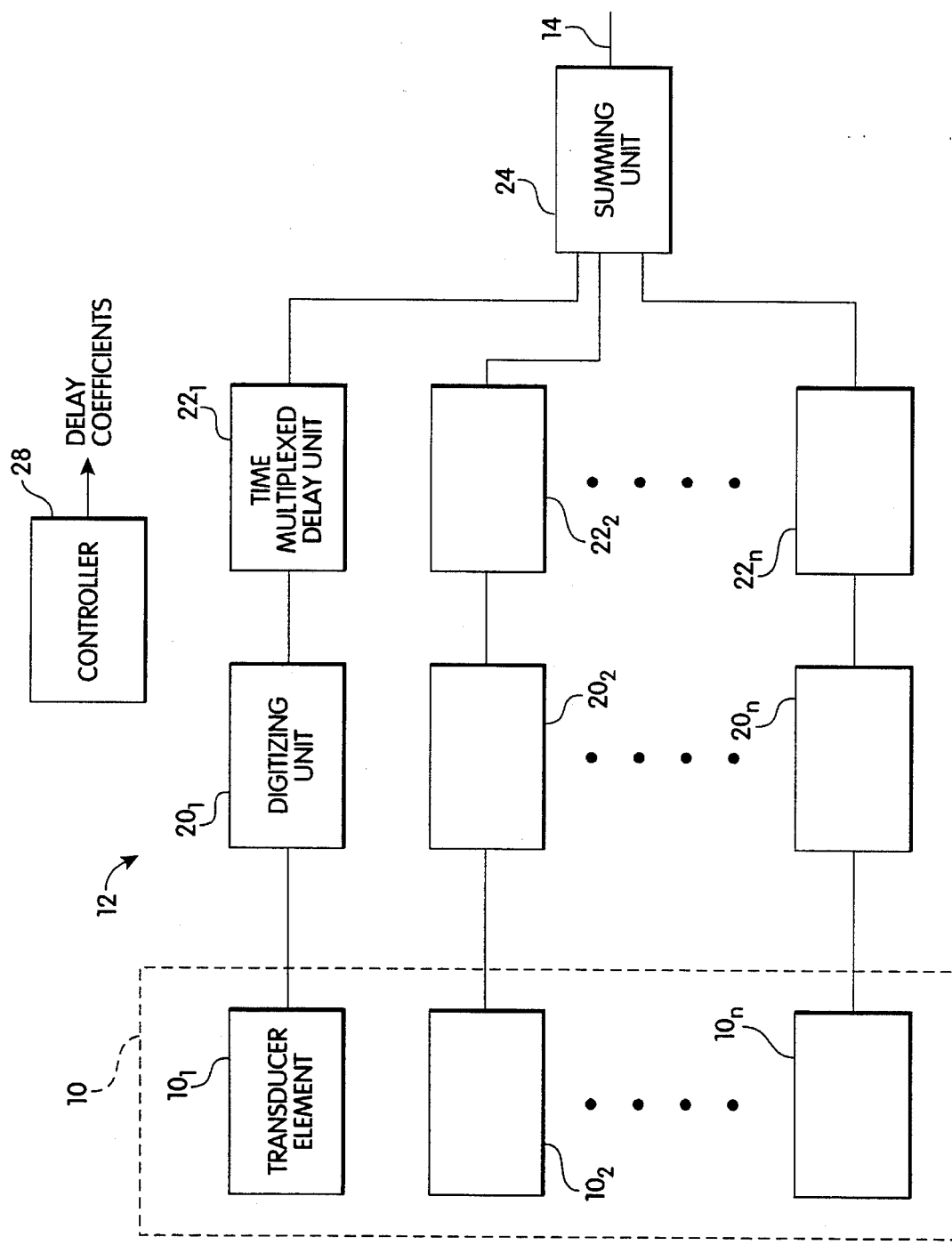
FIG. 1 is a block diagram of a digital phased array ultrasound beamformer in accordance with the present invention.

A simplified block diagram of an ultrasound transducer array and a digital phased array ultrasound beamformer in accordance with the invention is shown in FIG. 1. A phased array ultrasound transducer 10 includes transducer elements $10_1$, $10_2$, . . . $10_n$. The transducer elements are typically arranged in a linear or curvilinear array. The ultrasound transducer 10 typically includes up to 128 transducer elements.

Figure 3:
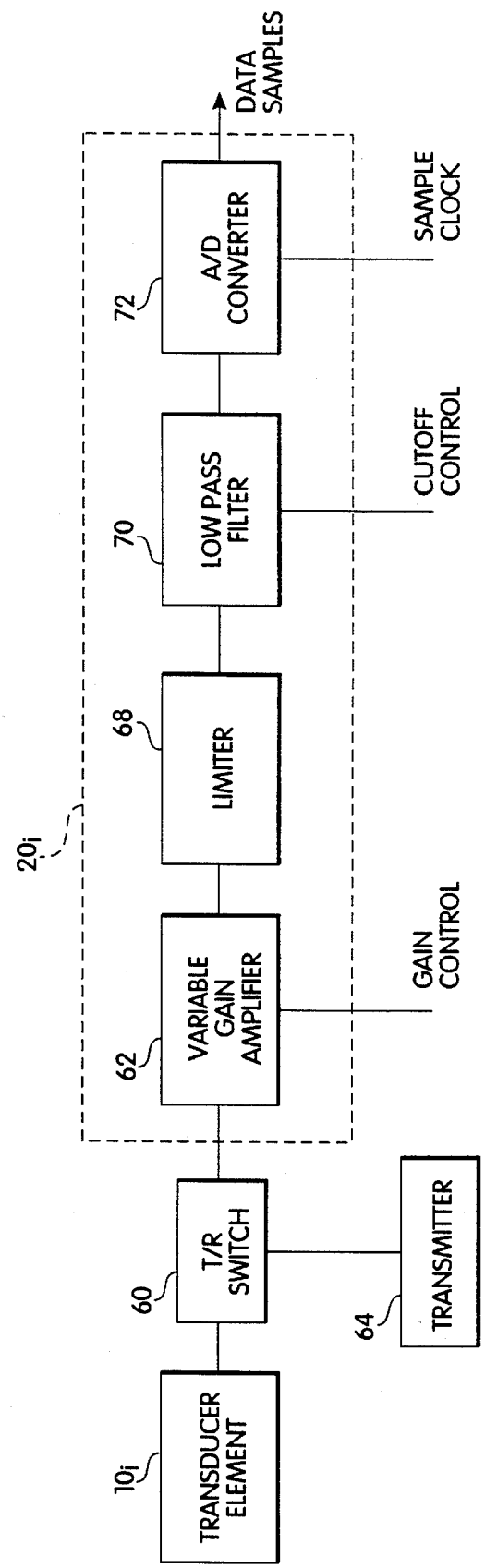
FIG. 3 is a block diagram of the digitizing unit for one processing channel of the ultrasound beamformer shown in FIG. 1, connected through a transmit/receive switch to a transducer element.

The ultrasound transducer 10 transmits ultrasound energy into an object being imaged and receives reflected ultrasound energy. In a medical ultrasound imaging system, reflections are received from various structures and organs within a region of the human body. The transmitter portion of the ultrasound scanner is omitted from FIG. 1 for simplicity, but is shown in FIG. 3. By appropriately delaying the pulses applied to each transducer element, a focused ultrasound beam is transmitted into the patient. The transmitted beam is focused and steered by varying the delays associated with each transducer element.

The reflected ultrasound energy from a given point within the patient's body is received by the transducer elements at different times. Each of the transducer elements $10_1, 10_2, \ldots 10_n$ converts the received ultrasound energy to an electrical signal which is supplied to a receive beamformer 12. The beamformer 12 processes the electrical signals so as to control the receive sensitivity pattern and to thereby effect focusing and steering of the received ultrasound energy. The depth and direction of the focal point relative to the ultrasound transducer 10 can be varied dynamically with time by appropriately delaying the received signals from each of the transducer elements. The beamformer 12 includes a separate processing channel for each transducer element.

The ultrasound transducer, the transmitter and the receive beamformer are part of a phased array ultrasound scanner which transmits and receives ultrasound energy along a plurality of scan lines. Sector scan patterns, linear scan patterns and other scan patterns known to those skilled in the art can be utilized. The output of the beamformer 12 is a series of digital data samples which represent the received ultrasound energy along each scan line. A beamformer output 14 is processed according to known techniques to produce an ultrasound image of the region being scanned.

Respective electrical signals from the transducer elements $10_1, 10_2, \ldots 10_n$ are applied to individual processing channels of the beamformer 12. Each processing channel includes a digitizing unit $20_i$ and a time multiplexed delay unit $22_i$, where i varies from 1 to n. The output of transducer element $10_1$ is applied to the input of digitizing unit $20_1$, and the output of digitizing unit $20_1$ is applied to the input of time multiplexed delay unit $22_1$. Similarly, the output of transducer element $10_2$ is applied to the input of digitizing unit $20_2$, and the output of digitizing unit $20_2$ is applied to the input of time multiplexed delay unit $22_2$. The outputs of time multiplexed delay units $22_1, 22_2, \ldots 22_n$ are applied to the inputs of a summing unit 24. A controller 28 supplies delay coefficients and other control information to each processing channel. In general, each digitizing unit $20_i$ converts the analog signal from the transducer element to a series of digital samples representative of the analog signal. The time multiplexed delay unit $22_i$ applies a delay to each digital sample. The delay is selected such that the receive sensitivity pattern is steered in a desired direction and is focused at a desired depth.

In accordance with an important feature of the present invention, the delays applied to the digital samples correspond to multiple receive beams and are time multiplexed so that the stream of delayed digital samples simultaneously represents the multiple receive beams. Thus, the beamformer 12 performs time multiplexed processing of multiple receive beams. The number of receive beams that can be processed in a time multiplexed beamformer depends on the clock rate of the beamformer and the frequency of the transducer being used. All the receive beams processed by the time multiplexed beamformer must be within the transmitted pattern of ultrasound energy. This requirement can be met by transmitting a single beam that is sufficiently broad to include all receive beams, by transmitting multiple beams simultaneously or by transmitting multiple beams in rapid succession.

In an ultrasound imaging system, different transducers with different frequencies may be used for different applications. The clock rate for the beamformer must be sufficient to meet the Nyquist requirement for the highest frequency transducer to be used, along with any guard band that may be utilized. For example, when the highest frequency transducer is a 10 MHz phased array transducer with 100% fractional bandwidth (5 MHz to 15 MHz), a clock raze of 40 MHz may be used. The digital beamformer operating at a clock rate of 40 MHz is capable of processing one receive beam for the 10 MHz transducer. When the same clock rate is used, the beamformer can perform time multiplexed processing of two receive beams with a 5 MHz transducer, three receive beams with a 3.33 MHz transducer or four receive beams with a 2.5 MHz transducer. For lower frequency transducers, multiple receive beams can be processed without changing the clock rate and without replicating the hardware in the receive beamformer. Thus, depending on the transducer used, one to four receive beams can be processed by the beamformer. It will be understood that different numbers of beams can be processed simultaneously depending on the relation between the clock rate and the transducer frequency. As described below, by replicating a portion of the beamformer circuitry, additional beams can be processed.

Figure 2:
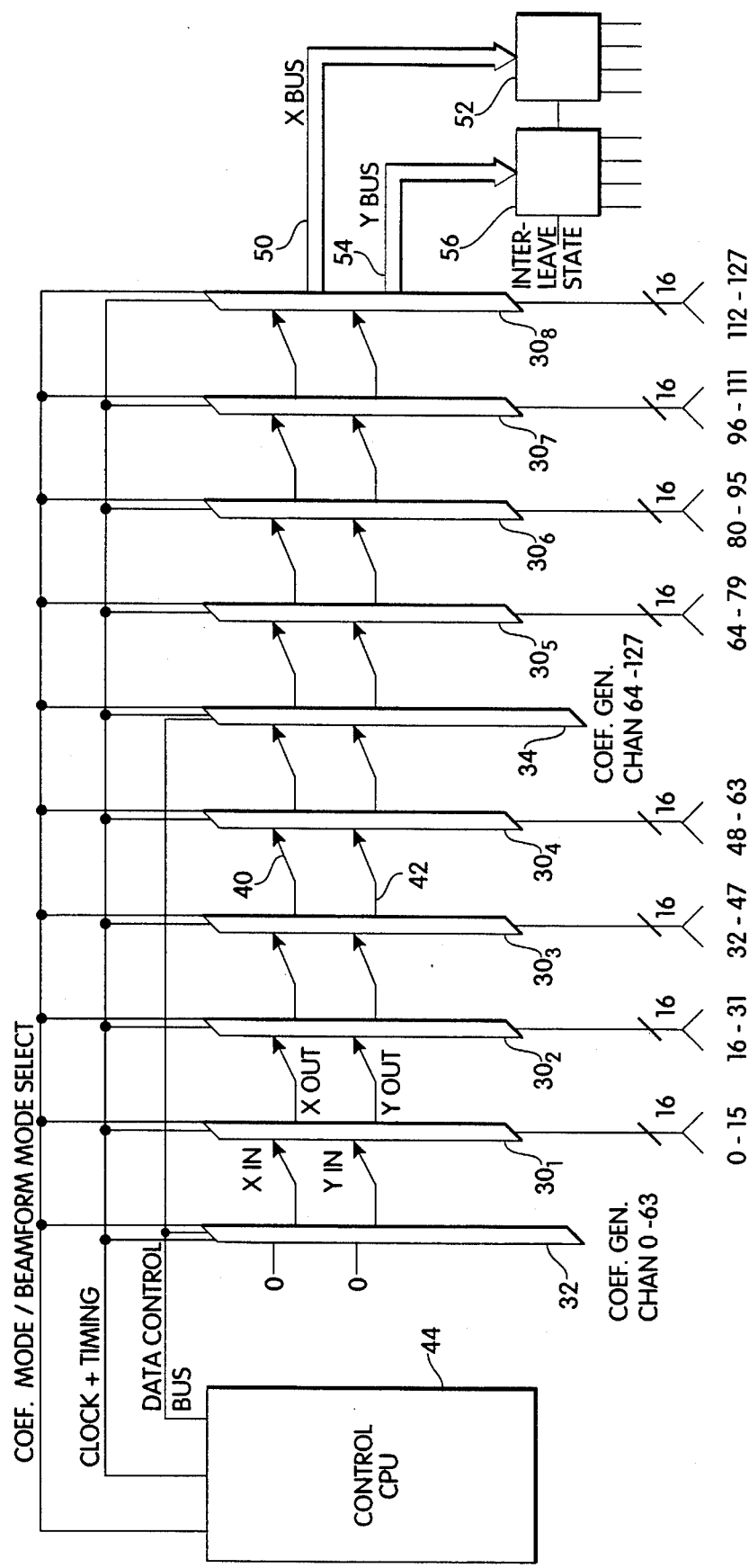
FIG. 2 is a schematic diagram of a preferred architecture for the ultrasound beamformer shown in FIG. 1.

A preferred architecture for the beamformer 12 is shown in FIG. 2. Receiver boards $30_1, 30_2, \ldots 30_8$ each process the signals from 16 transducer elements of the transducer 10. Eight boards are used with a preferred transducer having 128 transducer elements. A coefficient generator 32 supplies delay coefficients for the first four receiver boards $30_1, 30_2, 30_3$ and $30_4$, and a coefficient generator 34 supplies delay coefficients for the last four receiver boards $30_5, 30_6, 30_7$ and $30_8$. Each receiver board includes the digitizing unit $20_i$ and the time multiplexed delay unit $22_i$ for sixteen transducer elements. Each receiver board also includes a portion of the summing unit 24 as described below.

The receiver boards $30_1, 30_2, \ldots 30_8$ and coefficient generators 32 and 34 are interconnected by an X bus 40 and a Y bus 42. The buses 40 and 42 are daisy chained between boards, with clock synchronized registers in the path between each board, so that each receiver board drives only the following board. As a result, lead length problems and logic propagation delay problems are avoided. During receive, the X bus 40 carries delayed data samples for up to four time multiplexed primary beams, and the Y bus 42 carries delayed data samples for up to four time multiplexed neighbor beams. The coefficient generators 32 and 34 contain cache memories for storing delay coefficients and send delay coefficients to the related receiver boards on buses 40 and 42 prior to transmission of ultrasound energy. A control CPU 44 controls the coefficient generators 32 and 34 and the receiver boards $30_1, 30_2, \ldots 30_8$.

An X bus output 50 of the beamformer is input to a demultiplexer 52, and a Y bus output 54 is input to a demultiplexer 56. The demultiplexers 52 and 56 are controlled by an Interleave State signal which is synchronized with the time multiplexed digital samples on outputs 50 and 54. Each bus output is demultiplexed to provide up to four separate signals, each representing a different receive beam. The signal foe each receive beam is processed as known in the art to generate an ultrasound image. Since up to eight receive beams are generated simultaneously, the frame rate of the ultrasound image is increased by a factor of up to eight. As noted above, more or fewer beams can be processed within the scope of the present invention.

A block diagram of a preferred embodiment of the digitizing unit $20_i$ for each processing channel in the beamformer 12 of FIG. 1 is shown in FIG. 3. A transducer element $10_i$ is electrically connected to a transmit/receive switch 60. A first poet of the transmit/receive switch 60 is connected to the input of a variable gain amplifier 62. A transmitter 64 is connected to a second port of the transmit/receive switch 60. As is known in the art, the transmit/receive switch 60 protects the input to amplifier 62 when the transmitter 64 is energized. The amplifier 62 amplifies the low level analog signal from transducer element 10$_i$ and supplies an amplified signal to an input of a limiter 68. The gain control of amplifier 62 is used to effect time gain control (TGC) during receive and to control overall gain, as is known in the art. The output of limiter 68 is connected through a low pass filter 70 to the input of an analog-to-digital converter 72. The analog-to-digital converter 72 samples the transducer signal at a sample clock rate that is sufficient to meet the Nyquist requirement, along with any desired guard band, for the highest frequency transducer to be used in the system. As noted above, a preferred clock rate is about 40 MHz. The output of the analog-to-digital converter 72 is a stream of digital data samples at the sample clock rate.

The low pass filter 70 prevents aliasing of the data samples by high frequency components of the analog signal. The low pass filter 70 has a selectable cutoff frequency depending on the transducer frequency and the interleave factor used in the beamformer. For example, when a clock rate of 40 MHz and a 10 MHz transducer are used to form one beam, the low pass filter 70 may have a corner frequency at 15 MHz. When the same clock rate is used to perform time multiplexed processing of two receive beams with a 5 MHz transducer, the filter 70 may have a corner frequency of 7.5 MHz. Similarly, for three receive beams, the filter 70 may have a corner frequency of 5 MHz, and for four receive beams, the filter 70 may have a corner frequency of 3.75 MHz.

In the event that the analog-to-digital converter 72 is driven into saturation, harmonics will be generated. The harmonics can cause aliasing of the data samples and are not removed by the low pass filter 70. This problem is overcome by the limiter 68 which limits the analog signal supplied to analog-to-digital converter 72 at a level slightly below the level at which the analog-to-digital converter 72 saturates. As a result, harmonics caused by saturation of the analog-to-digital converter 72 are prevented.

Figure 4:
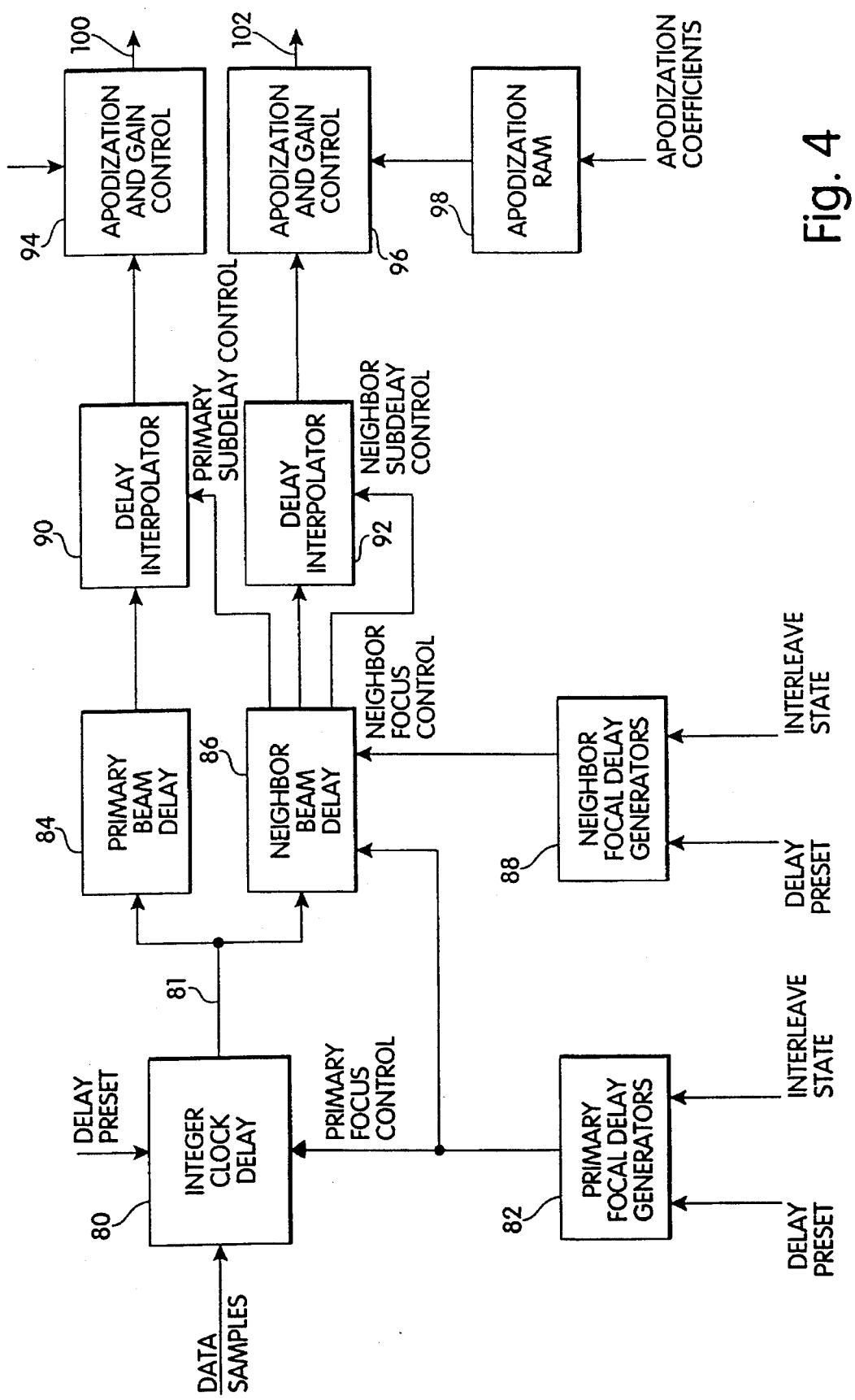
FIG. 4 is a block diagram of a first embodiment of the time multiplexed delay unit for one processing channel of the ultrasound beamformer shown in FIG. 1.

A block diagram of a first embodiment of the time multiplexed delay unit 22$_i$ for each processing channel is shown in FIG. 4. Data samples from the digitizing unit 20$_i$ (FIG. 3) are input to an integer clock delay 80. The integer clock delay applies to the data samples a delay that is quantized in increments equal to the sample clock period. The delays applied to the data samples correspond to multiple receive beams and are time multiplexed such that the output of the integer clock delay can be used for forming multiple receive beams. Thus, if the system is configured to process four receive beams, the output of integer clock delay 80 on a line 81 contains a stream of digital data samples which correspond to four receive beams. In a first clock cycle, the data sample is delayed by an amount required to form a first receive beam. In a second clock cycle, the second data sample is delayed by an amount required to form a second receive beam. In a third clock cycle, a third data sample is delayed by an amount required to form a third receive beam. In a fourth clock cycle, the fourth data sample is delayed by an amount required to form a fourth receive beam. This process is then repeated. The resulting data stream contains time multiplexed data samples that are simultaneously representative of four receive beams. The receive beams can have different focal points and different angles with respect to the transducer. However, the receive beams must fall within the pattern of transmitted ultrasound energy.

The delays applied by the integer clock delay 80 are controlled by primary focal delay generators 82, with one focal delay generator corresponding to each receive beam. The integer clock delay receives primary focus control signals from the primary focal delay generator 82.

The output of the integer clock delay is supplied on line 81 To the input of a primary beam delay 84 and to the input of a neighbor beam delay 86. The neighbor beam delay 86 receives focus control signals from the primary focal delay generators 82 and from neighbor focal delay generators 88. The primary beam delay 84 and the neighbor beam delay 86 are used to form a set of primary receive beams and a set of neighbor receive beams. Each neighbor receive beam is slightly offset in angle from a corresponding primary beam. The output of the primary beam delay 84 is a stream of time multiplexed data samples for forming up to four primary beams. The output of neighbor beam delay 86 is a stream of time multiplexed data samples for forming up to four neighbor beams. Thus, the primary beam delay 84 and the neighbor beam delay 86 permit the generation of additional receive beams, but at the expense of additional beamforming hardware. If a smaller number receive beams is acceptable, the neighbor beam circuitry can be eliminated.

The output of primary beam delay 84 is supplied to a delay interpolator 90, and the output of neighbor beam delay 86 is supplied to a delay interpolator 92. The function of the delay interpolators 90 and 92 is to delay each data sample by a selected subdelay that is quantized in increments of less than the sampling period. Thus, for example, each sample in the data stream can be delayed by 0, ¼ τ, ½ τ, or ¾ τ, where τ is the sampling period. The delay interpolators permit generation of high quality images without increasing the sampling clock rate. The delay interpolators 90 and 92 are time multiplexed in the same manner as the integer clock delay 80. The delays applied to the data samples are time multiplexed so that the outputs represent up to four receive beams simultaneously. The subdelay information for delay interpolators 90 and 92 is received from neighbor beam delay 86 as a primary subdelay control signal and a neighbor subdelay control signal, respectively.

The outputs of delay interpolators 90 and 92 are supplied to apodization and gain controls 94 and 96, respectively. The apodization and gain controls 94 and 96 comprise multipliers for adjusting the amplitudes of the data samples for each receive beam. The apodization information is contained in an apodization RAM 98 which supplies apodization and gain coefficients to the apodization and gain controls 94 and 96. The apodization information is loaded into RAM 98 from the coefficient generators 32 and 34. Application of apodization and gain coefficients to the controls 94 and 96 is synchronized to the receive beams by the Interleave State signal. The outputs 100 and 102 of the time multiplexed delay unit 22$_i$ each comprise a stream of time multiplexed data samples which simultaneously represent up to four receive beams. The output 100 represents up to four primary receive beams and the output 102 represents up to four neighbor receive beams. As shown in FIG. 1, the outputs for each processing channel are summed by the summing unit 24 to provide the beamformer output 14. Operation of the summing unit 24 is described in detail below.

Figure 5:
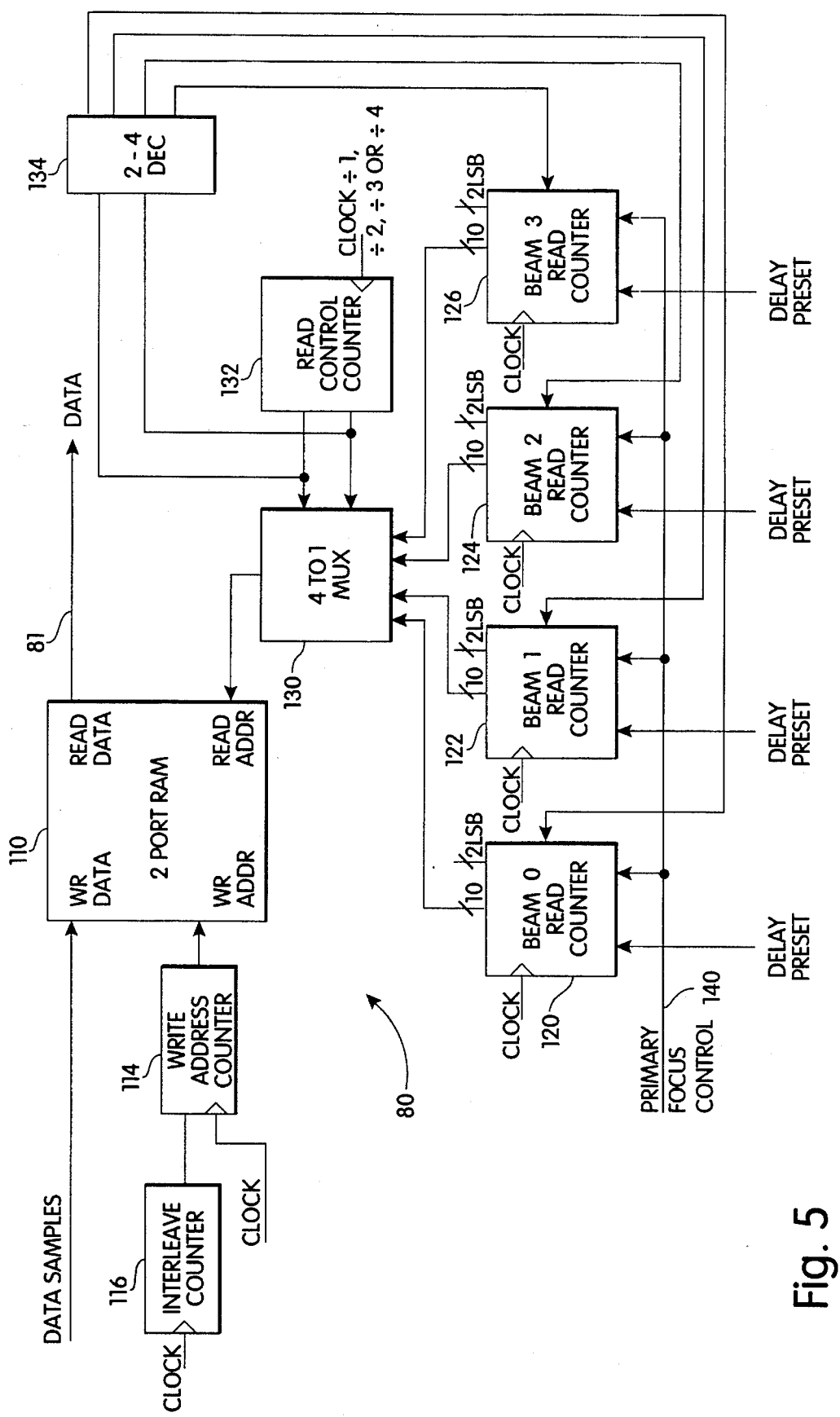
FIG. 5 is a block diagram of the integer clock delay shown in FIG. 4.

A block diagram of an example of the integer clock delay 80 shown in FIG. 5. Data samples from the analog-to-digital converter 72 (FIG. 3) are input to a two-port random access memory (RAM) 110. The two-port RAM 110 permits simultaneous writing and reading of data. In a preferred embodiment, the two-port RAM 110 has 1024 locations, each with a sufficient number of bits to store the data samples from the analog-to-digital converter 72. In a preferred embodiment, 10 bit data samples are utilized. The two-port RAM 110 and associated circuitry apply time multiplexed delays to the data samples. The two-port RAM 110 supplies at its output a stream of data samples for forming multiple receive beams.

The two-port RAM 110 operates as a "circular" memory. For writing data samples into the memory, locations in the RAM 110 are sequentially addressed, and the data samples are stored in the addressed locations. When the RAM 110 is full, the write address recycles to the first location, and the next data sample is written in the first location. The write addresses are again sequenced, and data samples are written over the previously stored data samples.

The data samples are delayed by reading data from addresses that offset from the write addresses. The read addresses are also sequenced to provide a continuous stream of output data that is delayed with respect to the input data. Thus, for example, when the read address is offset from the write address by 10 memory locations, the data samples supplied at the output of two-port RAM 110 are delayed by 10 clock cycles with respect to the input data samples.

In order to perform dynamic focusing during receive, the delay applied to the data samples must be varied dynamically. Changes in delay are accomplished by changing the difference between the write address and the read address in two-port RAM 110. Thus, for example, the difference between the write address and the read address may be changed from 10 locations, which corresponds to a delay of 10 clock cycles, to 11 locations, which corresponds to a delay of 11 clock cycles. Typically, the required delay remains constant for several cycles and then is incremented by one clock cycle. As described below, incrementing of the delay is effected by "stalling" a read address counter. This effectively changes the difference between the write address and the read address. Subdelays quantized in increments of less than one clock cycle are provided by the delay interpolators as described below.

As indicated above, the integer clock delay 80 is capable of processing multiple receive beams in a time multiplexed manner. Furthermore, the number of receive beams is selectable. In a preferred embodiment, one, two, three or four receive beams can be processed. The number of receive beams typically depends on the transducer being used with the ultrasound imaging system. Thus, for example when a 10 MHz transducer is used, one receive beam can be processed, and when a 2.5 MHz transducer is used, four receive beams can be processed. The number of receive beams is set for a particular transducer type and is indicated by an "Interleave Factor" signal.

The two-port RAM 110 is addressed by a write address counter 114, which is synchronized to the system clock. A counter 116 supplies a count enable signal to the write address counter 114. The counter 116 is synchronized to the system clock and divides the system clock frequency by one, two, three or four depending on the desired number of receive beams (the interleave factor). When the interleave factor is one, corresponding to one receive beam, the write address counter 114 is incremented by each system clock pulse. When the interleave factor is four, the write address counter 114 is incremented by every fourth system clock pulse. Thus, for an interleave factor of one, every data sample is stored in the two-port RAM 110. For an interleave factor of four, every fourth data sample is stored in the two-port RAM 110. No information is lost because the analog signal from the transducer element has a lower maximum frequency, and the required sampling rate to meet the Nyquist requirement is lower.

The read address for the two-port RAM 110 is supplied by read counters 120, 122, 124 and 126. One of the read counters corresponds to each receive beam. The outputs of the read counters 120, 122, 124 and 126 are supplied through a four-to-one multiplexer 130 to the read address input of two-port RAM 110. The state of the multiplexer 130 is controlled by a read control counter 132. The outputs of read control counter 132 are supplied to the control inputs of multiplexer 130 and to the inputs of a two-line to four-line decoder 134. The outputs of decoder 134 are supplied to the enable inputs of read counters 120, 122, 124 and 126, respectively.

Each read counter 120, 122, 124, 126 receives an enable signal from the decoder 134, an initial delay preset from the coefficient generator 32 or 34 (FIG. 2), a primary focus control signal from the primary focal delay generators 82 (FIG. 4), and the system clock. The initial delay preset establishes the initial delay to be applied to the data samples for a given receive beam. The primary focus control signal contains stall commands which change the applied delay.

In an example of the integer clock delay 80, the two-port RAM 110 has 1024 locations. Each of the read counters 120, 122, 124 and 126 is a 12-bit incrementor and receives a 12-bit initial delay preset. The ten most significants bits of the selected read counter are supplied through the multiplexer 130 to the read address input of two-port RAM 110. This configuration permits the data samples to be delayed by up to 1024 clock cycles. The two least significant bits of each read counter represent subdelays of less than one clock cycle and are not used in the integer clock delay. The subdelays are applied by the delay interpolator 90, as described below. In a preferred embodiment, total delays are quantized in increments of one quarter clock cycle, and one clock cycle represents four delay quanta. When no change in delay is required for a particular receive beam, the stall command is inactive, and the corresponding read counter is incremented by 4 (which corresponds to one clock cycle). This causes the read address applied to the RAM 110 to be incremented by one location. When a change in delay is required for a particular receive beam, the stall command is active, and the corresponding read counter is incremented by 3. Although this corresponds to ¾ of a clock cycle, the read address applied to the RAM 110 is stalled (remains the same), and the subdelay applied by delay interpolator 90 is adjusted to effect a total change of one delay quanta.

Figure 6:
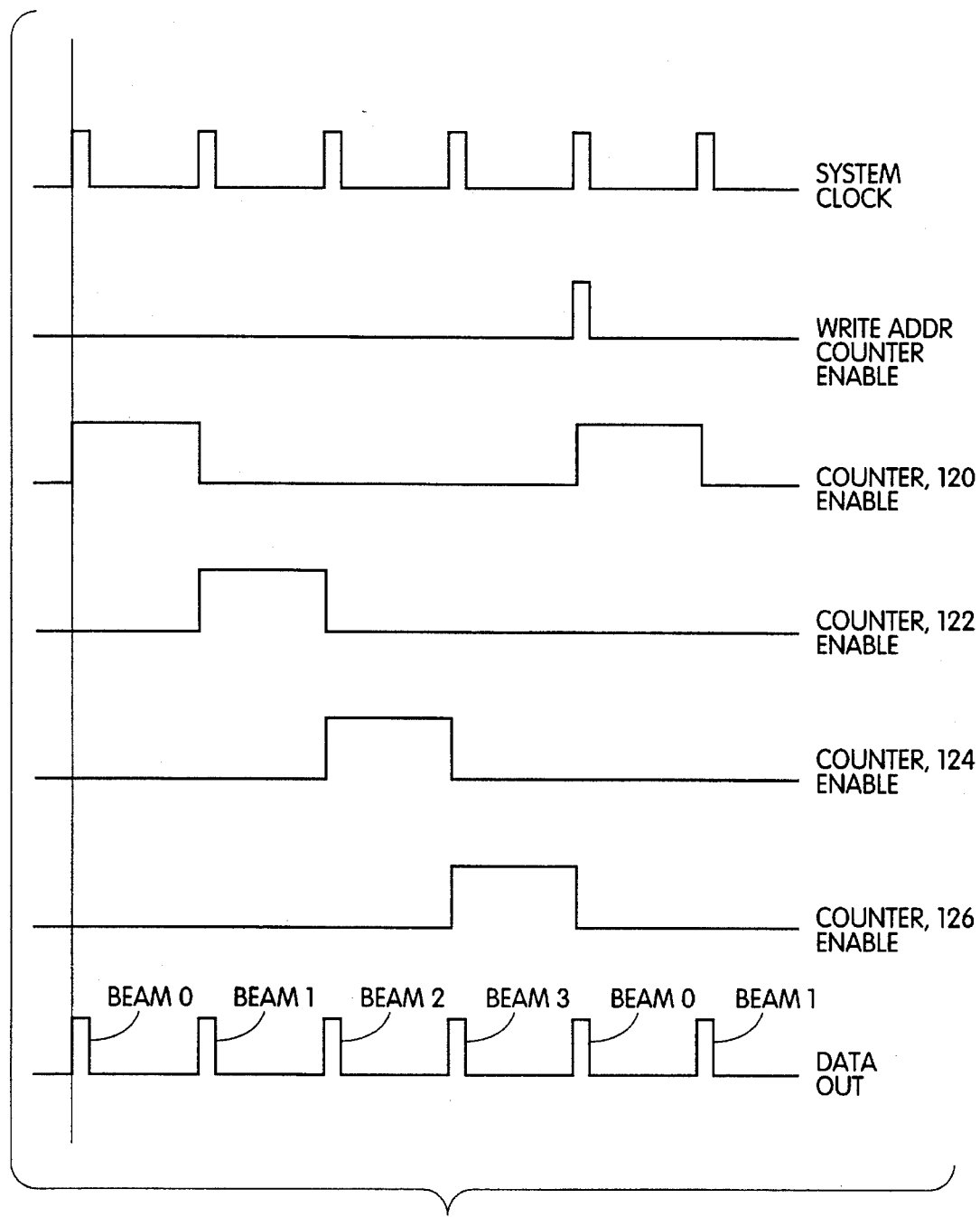
FIG. 6 is a timing diagram that illustrates time multiplexed operation of the integer clock delay shown in FIG.

Operation of the integer clock delay 80 is described with reference to FIG. 6, which illustrates the timing for processing four receive beams. As noted previously, the write address counter 114 is enabled to change states on every fourth system clock pulse. The two-port RAM 110 contains data samples which represent the input signal over a prescribed time period. During a first clock cycle, the multiplexer 130 selects read counter 120, and the read address stored therein is applied to the read address input of two-port RAM 110. Read address counter 120 contains a read address which represents the required delay for a first receive beam. The data sample stored at the address specified by read counter 120 is supplied by RAM 110 on line 81. During a second clock pulse, the multiplexer 130 selects the output of read counter 122, and the read address stored therein is applied to the RAM 110. Read counter 122 contains a read address which represents the required delay for a second receive beam. The data sample stored at the address specified by read counter 122 is supplied by RAM 110 on line 81. Similarly, the outputs of read counters 124 and 126 are applied to the RAM 110 during third and fourth clock cycles, respectively, and data samples representative of third and fourth receive beams are supplied by RAM 110 on line 81. The resultant output of RAM 110 is a serial data stream in which data samples for forming four receive beams are time multiplexed.

As indicated above, the read counters 120, 122, 124 and 126 receive initial delay presets from the coefficient generators 32, 34 and stall commands from the primary focal delay generators 82. A focal delay generator is provided for each read counter. The stall commands may be time multiplexed on a line 140 to reduce the number of interconnections between the integer clock delay 80 and the primary focal delay generators 82, which may be packaged in different integrated circuits. The addressing of the stall commands is controlled by the enable signals generated by the decoder 134.

As known in the art, the general equation for the delay applied to each element in an ultrasound array is a function of the element position in the array relative to a reference such as the center element, the angle of the receive scan line and the range, or depth, of the focal point. For a given scan line, the element X position and scan line angle θ typically remain fixed, and the range is a function of time in order to effect dynamic focusing. During dynamic focusing, the required delay for each transducer element increases.

In the present invention, an increase in delay corresponds to stalling one of the read counters. As discussed above, stalling of the read counter causes an increase in the difference between the read address and the write address, thus increasing the delay applied to the data samples. The initial delay preset for each read counter represents the delay for the particular transducer element (X position) and scan line angle. The delay required for dynamic focusing along the given scan line is determined by the respective primary focal delay generators 82. Based on the transducer element position, the scan line angle and the delay equation, each focal delay generator determines the times when the required delay, as represented by the contents of the corresponding read counter, must be changed and issues stall commands. The stall commands are synchronized with the system clock. The focal delay generators are described in detail in a copending application entitled "Focal Delay Generator For Digital Phased Array Ultrasound Beamformer", Assignee's Docket No. 1092274, which is hereby incorporated by reference.

As noted previously, the read counter is incremented by four when a stall is not required. Since the two least significant bits of the read counter are not applied to the two-port RAM 110, the addition of four to the read counter causes the read address in RAM 110 to be incremented by one, and the applied delay remains fixed. When a stall is required, the read counter is incremented by three. Since the two least significant bits of the read counter are not applied to the RAM 110, the effect is to stall the read counter at the same read address in RAM 110 and thereby lengthen the coarse delay by one sample period. As will be described below, the delay interpolator 90 adjusts the delay by a fraction of the sample clock period so that the total delay changes by ¼ of the sample clock period (one delay quanta) when a stall command is given.

Figure 7:
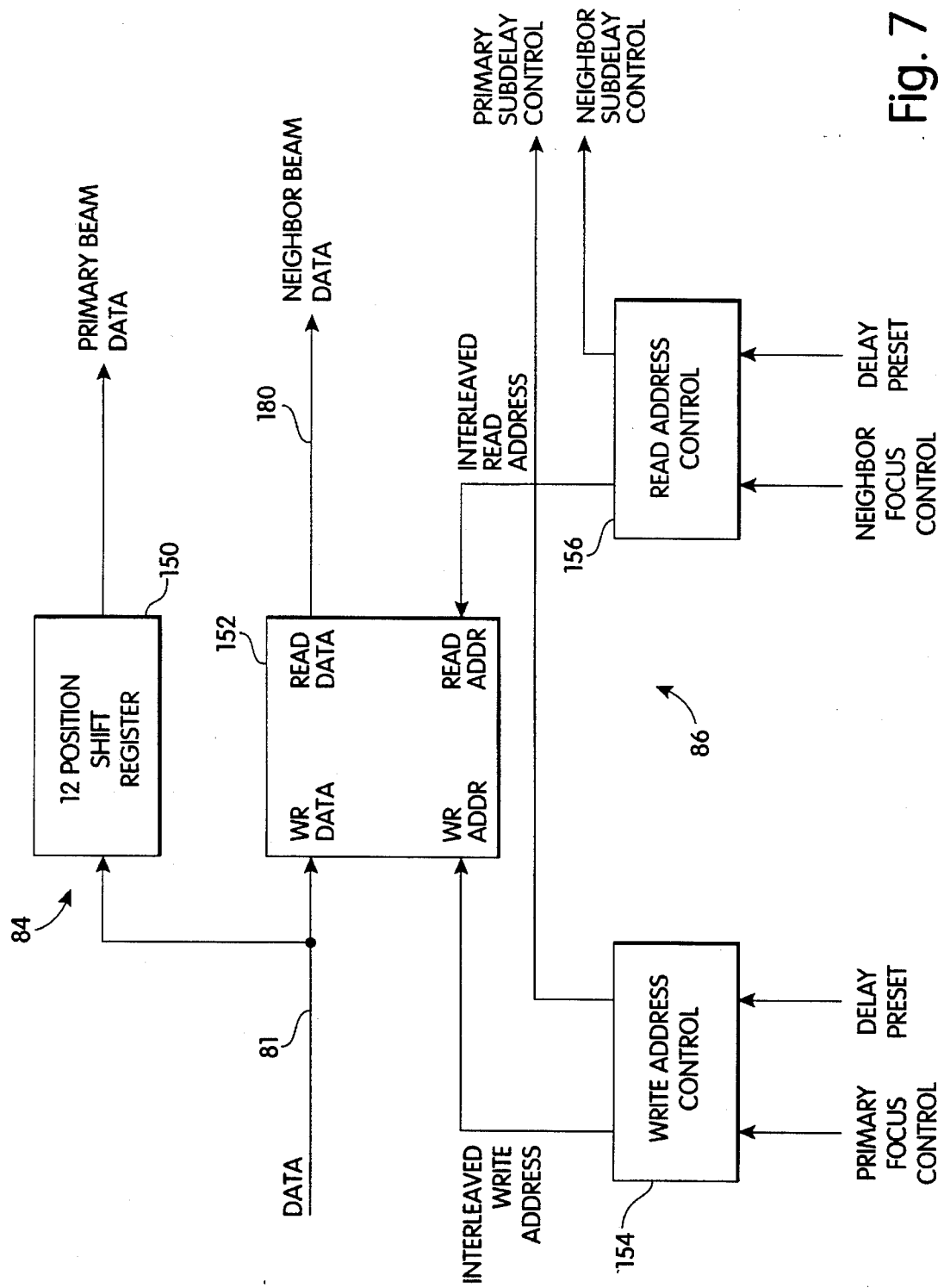
FIG. 7 is a block diagram of the primary beam delay and the neighbor beam delay shown in FIG. 4.

A block diagram of an example of the primary beam delay 84 and the neighbor beam delay 86 is shown in FIG. 7. The concept of primary beams and neighbor beams is used to increase the number of receive beams processed simultaneously with only a modest increase in required circuitry. Each primary receive beam has a corresponding neighbor receive beam that is slightly displaced in angle from the primary beam. The displacement in angle corresponds to a small difference in delay. In the example shown in FIG. 8, one to four primary beams and one to four neighbor beams can be processed.

The primary beam delay 84 is preferably implemented as a 12-stage shift register 150, which adds a fixed delay of 12 clock cycles to each data sample in each of the primary beams. It will be understood that addition of the same fixed delay to the data samples for all of transducer elements has no effect on steering or dynamic focus. The shift register 150 preferably includes a number of stages that is divisible by the number of receive beams that can be processed by the beamformer (one, two three or four in the preferred embodiment).

The neighbor beam delay 86 includes a two-port RAM 152, typically having 24 locations. The data samples supplied by RAM 110 (FIG. 5) on line 81 are applied to the write data input of two-port RAM 152 and to the first stage of shift register 150. The delay associated with the neighbor beams is 12±12 clock cycles with respect to the primary beams. The neighbor beam delay 86 removes the stall commands applied to the primary beams and applies stall commands required for processing the neighbor beams.

A write address control 154 supplies an interleaved write address to the write address input of two-port RAM 152. The write address control 154 also supplies a primary subdelay control to delay interpolator 90 (FIG. 4). The primary focal delay generators 82 (FIG. 4) supply a primary focus control to write address control 154. A read address control 156 supplies an interleaved read address to the read address input of two-port RAM 152. The read address control 156 also supplies a neighbor subdelay control to delay interpolator 92 (FIG. 4). The neighbor focal delay generators 88 (FIG. 4) supply a neighbor focus control to read address control 156. The write address control 154 and the read address control 156 receive delay presets from the coefficient generators 32, 34 (FIG. 2).

Figure 8:
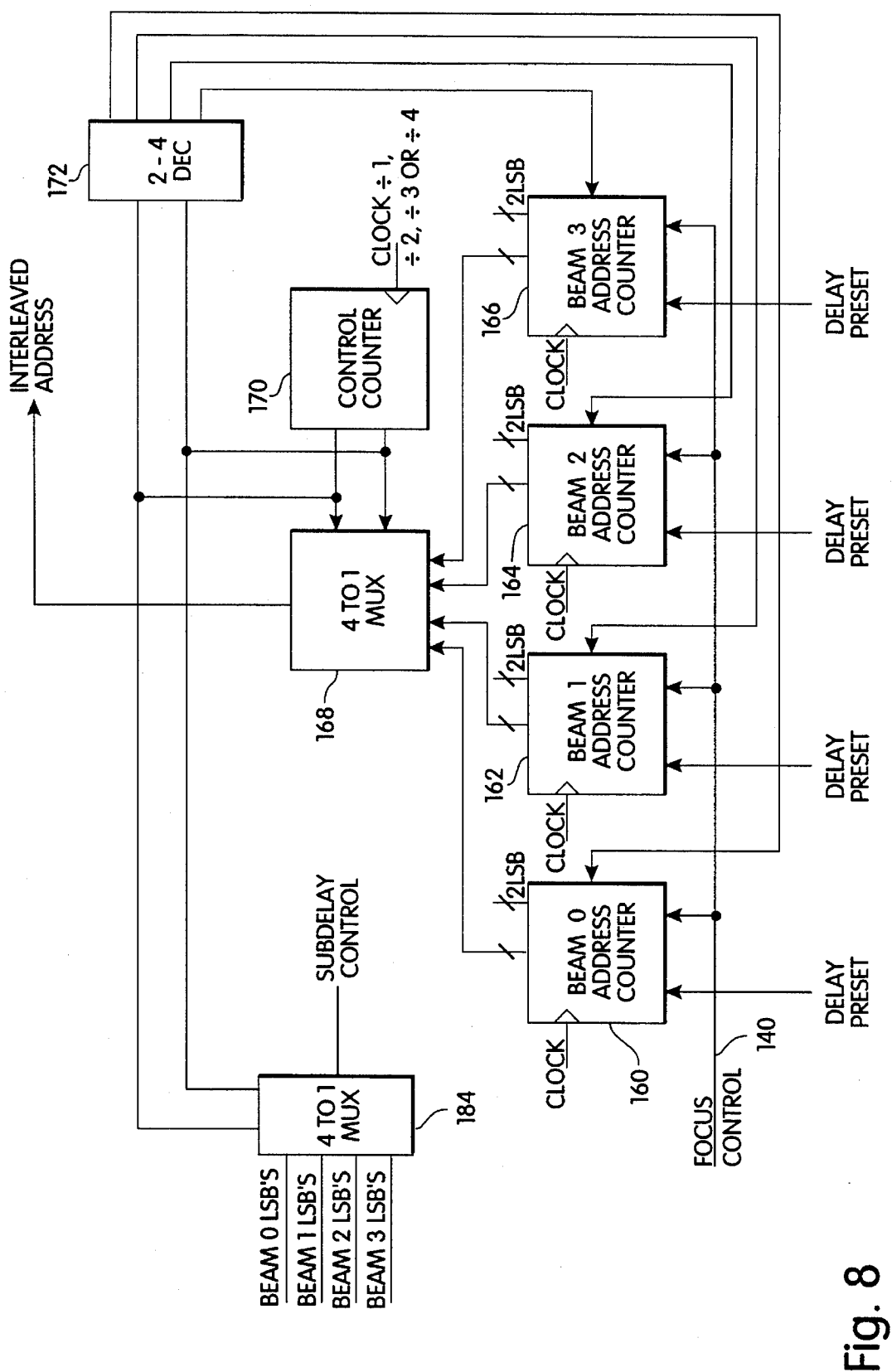
FIG. 8 is a block diagram representative of the write address control and the read address control shown in FIG. 7.

An example of a circuit suitable for implementation of the write address control 154 and the read address control 156 is shown in FIG. 8. Address counters 160, 162, 164 and 166 have outputs coupled to a four-to-one multiplexer 168 to provide an interleaved address to two-port RAM 152.

In the case of the write address control 154, the interleaved address is a write address, and in the case of the read address control 156, the interleaved address is a read address. Each address counter corresponds to one of the receive beams. The state of multiplexer 168 is controlled by a control counter 170. The state of control counter 170 represents an Interleave State signal, which indicates the receive beam currently being processed. Thus, when the data sample on line 81 represents receive beam 0, the Interleave State signal provided by control counter 170 causes the address counter 160 to be selected. The control counter 170 continuously sequences through the receive beams being processed. Each of the address counters 160, 162, 164 and 166 includes a MOD 24 counter, which corresponds to the 24 locations in RAM 152, and two additional stages for delay interpolation. The outputs of each MOD 24 counter are supplied to the multiplexer 168. The outputs of control counter 170 are supplied to a two-to-four line decoder 172. The outputs of decoder 172 are enable inputs for the address counters 160, 162, 164 and 166. Each of the address counters receives a focus control signal and an enable signal synchronized with the Interleave State signal generated by control counter 170. The primary focus control signal is applied to the counters in write address control 154, and the neighbor focus control signal is applied to the counters in read address control 156. As described above, the focus control signals contain stall commands which advance the enabled counter by four delay quanta for a constant delay or advance the enabled counter by three delay quanta to change the delay.

The contents of the enabled counter in write address control 154 are applied to the write address input of two-port RAM 152 in synchronism with the data samples for the corresponding receive beams. Since the counters in write address control 154 receive the same stall commands as read counters 120, 122, 124 and 126 (FIG. 5), the stall commands cancel and the data stored in two-port RAM 152 does not include the delay associated with the stall commands of the primary focus control signal.

The read address control 156 can also be implemented by the circuit shown in FIG. 8. It will be understood that separate circuits are used to implement the write address control 154 and the read address control 156. The outputs of the address counters 160, 162, 164 and 166 are coupled through multiplexer 168 to the read address input of two-port RAM 152. The multiplexer 168 is controlled by the Interleave State signal generated by control counter 170 as described above. Each counter in the read address control 156 includes a MOD 24 counter, with one state corresponding to each location in RAM 152, and two additional stages for delay interpolation. Each counter in read address control 156 receives an enable signal synchronized to the Interleave State signal and a neighbor focus control signal from neighbor focal delay generators 88 (FIG. 4). The neighbor focus control signal contains stall commands for each of the address counters and is synchronized to the Interleave State signal. Thus, the counters in read address control 156 are controlled in accordance with the stall commands for the neighbor beams. The output of the two-port RAM 152 on line 180 contains time multiplexed data samples representative of one to four neighbor receive beams.

In summary, the delays for the primary beams are applied to the data samples by the two-port RAM 110 (FIG. 5). The data samples from RAM 110 are delayed by an additional 12 clock cycles by shift register 150 to produce primary beam data samples on output line 154. The two-port RAM 152 and associated write address control 154 and read address control 156 remove the stalls required by the primary beams and apply stalls required by the neighbor beams to provide neighbor beam data samples on output line 180.

The two least significant bits of each of the address counters 160, 162, 164 and 166 are input to a four-to-one multiplexer 184, which is controlled by the Interleave State signal generated by control counter 170. The two least significant bits of each of the address counters 160, 162, 164 and 166 represent the subdelay, or fractional delay, required by each beam. The output of multiplexer 184 is a time multiplexed subdelay control signal. The subdelay control signal output of write address control 154 represents the subdelays for each primary beam and is applied to delay interpolator 90 (FIG. 4). The subdelay control signal output of read address control 156 represents the subdelay for each neighbor beam and is applied to delay interpolator 92 (FIG. 4).

Figure 9:
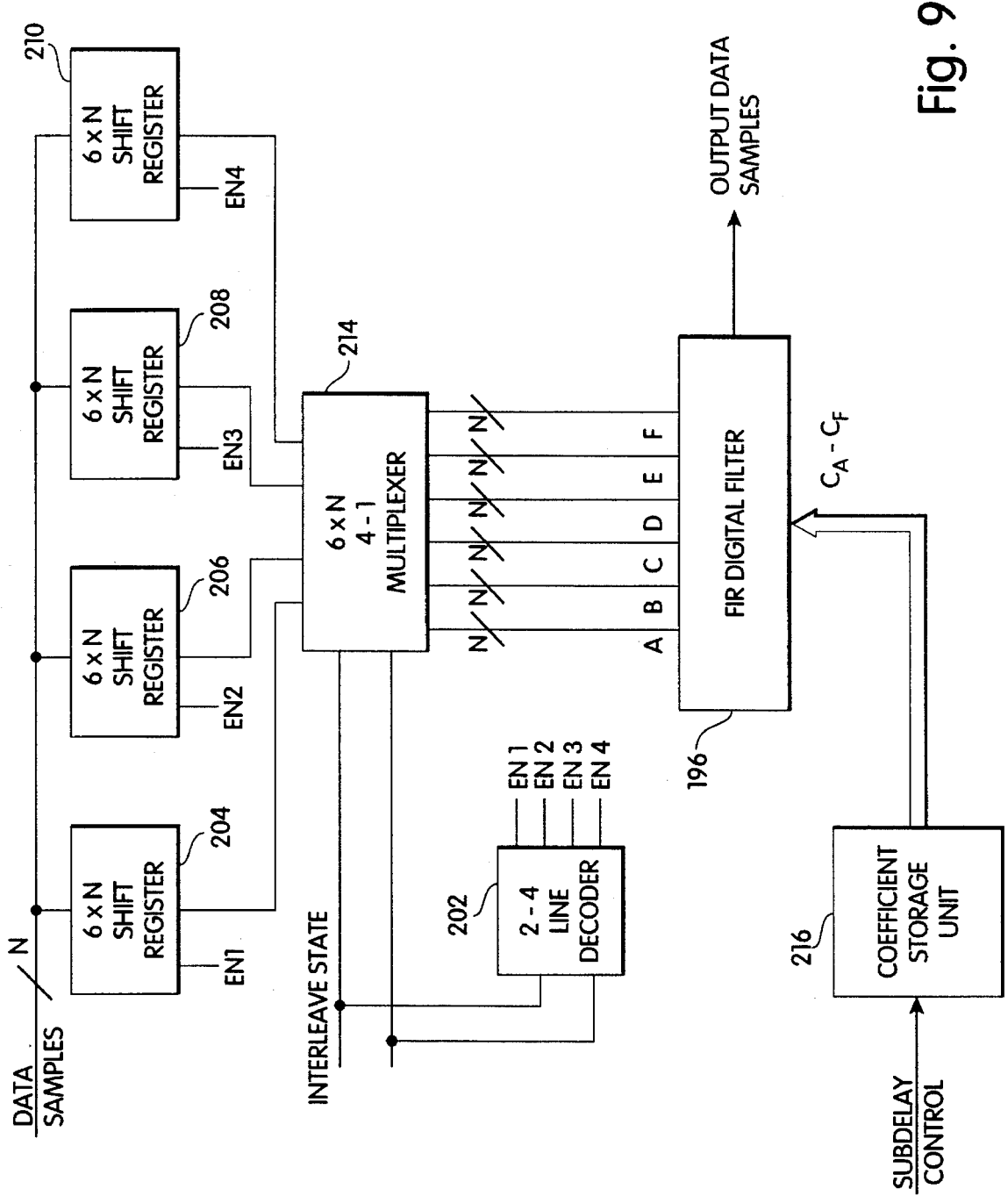
FIG. 9 is a block diagram representative of each delay interpolator shown in FIG. 4.

A block diagram of a preferred time multiplexed delay interpolator is shown in FIG. 9. The delay interpolator includes a finite impulse response (FIR) digital filter 196 having different selectable delays that are quantized in delays less than the sampling clock period. The FIR digital filter is designed to have a flat amplitude response and a linear delay as a function of frequency. Different delays are obtained by applying different filter coefficients to the FIR digital filter. The FIR digital filter for delay interpolation has an even number of stages and is symmetrical. In a preferred embodiment, the FIR digital filter 196 has six stages and produces delays of 0, ¼, ½ and ¾ of the sampling period. A preferred FIR digital filter 196 for delay interpolation is disclosed in a copending application entitled "Delay Interpolator For Digital Phased Array Ultrasound Beamformer", Assignee's Docket No. 1092185, which is hereby incorporated by reference.

The FIR digital filter delay interpolator can be utilized in the time multiplexed beamformer for time multiplexed processing of multiple receive beams because it does not contain internal feedback. The data for each beam is processed independently through the FIR digital filter.

The time multiplexed data samples from the primary beam delay 84 or the neighbor beam delay 86 are synchronized to the Interleave State signal. The Interleave State signal is decoded by a two-to-four line decoder 202 to provide enable signals EN1, EN2, EN3 and EN4. The enable signals indicate which beam is being processed at any instant of time. Thus, for example when enable signal EN1 is active, the data sample represents beam 0. The data samples are input in parallel to shift registers 204, 206, 208 and 210. In the embodiment where the FIR digital filter 196 includes six stages, each of the shift registers includes six stages, each of N bits, where N is the number of bits in each data sample. The shifting of data samples into registers 204, 206, 208 and 210 is controlled by enable signals EN1, EN2, EN3 and EN4. During a first clock cycle, enable signal EN1 is active, and a data sample representative of beam 0 is loaded into register 204. During a second clock cycle, enable signal EN2 is active, and a data sample representative of beam 1 is loaded into shift register 206. During a third clock cycle, enable signal EN3 is active, and a data sample representative of beam 2 is loaded into shift register 208. During a fourth clock cycle, enable signal EN4 is active, and a data sample representative of beam 3 is loaded into shift register 210. This process is repeated continuously so that each of the shift registers contains six consecutive samples of one of the four receive beams. Thus, register 204 contains six consecutive samples of beam 0, registers 206 contains six consecutive samples of beam 1, etc.

The outputs of registers 204, 206, 208 and 210 are supplied to a four-to-one multiplexer 214. Each of the four inputs of multiplexer 214 contain six data samples, each of N bits. The multiplexer 214 is controlled by the Interleave State signal. The output of multiplexer 214 is six data samples A–F, each of N bits, representative of one of the time multiplexed receive beams. The data samples A–F from multiplexer 214 are supplied to the inputs of the FIR digital filter 196. Filter coefficients $C_A$, $C_B$, $C_C$, $C_D$, $C_E$ and $C_F$ are supplied to FIR digital filter 196 from a coefficient unit 216, which can be a random access memory. A set of coefficients corresponding to a desired subdelay is addressed in the coefficient storage unit 216 by the subdelay control signal from neighbor beam delay 86 (FIG. 4). Each desired subdelay requires a different set of filter coefficients $C_A$–$C_F$.

In the FIR digital filter 196, the filter coefficients are multiplied by the six data samples A–F, respectively, and the results are summed to provide an output data sample. As noted above, the delay interpolator delays the digital samples by selected delays that are quantized in increments less than the sampling clock period. In a preferred embodiment, the delay interpolator produces delays of 0, ¼, ½ and ¾ of the sampling clock period. Thus, the output of the FIR digital filter 196 is a stream of data samples containing time multiplexed data for forming up to four receive beams. The data samples are delayed by an integer number of clock cycles by integer clock delay 80 and are delayed by subdelays of less than the sampling clock period by the respective delay interpolators 90 and 92.

Figure 10:
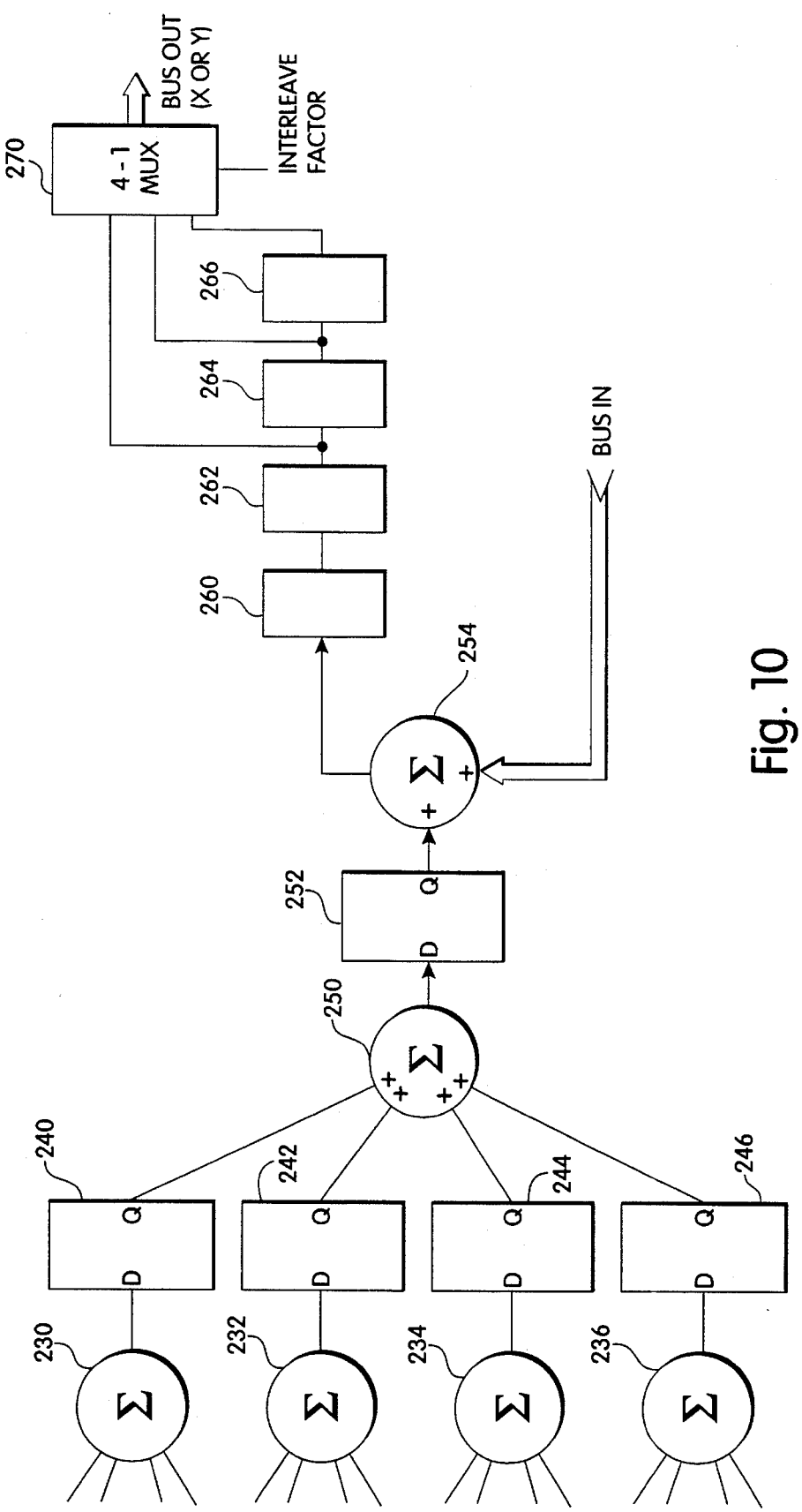
FIG. 10 is a block diagram of a portion of the summing unit shown in FIG. 1.

A portion of the summing unit 24 (FIG. 1) is shown in FIG. 10. The summing circuit shown in FIG. 10 sums the output of 16 processing channels of the receive beamformer. As indicated above, a typical phased array ultrasound transducer may include 128 transducer elements, thus requiring 128 processing channels in the beamformer. In the preferred architecture shown in FIG. 2, each receiver board processes the signals from 16 elements of the transducer array, and each receiver board includes the summing circuit shown in FIG. 10 for summing the 16 channels. The outputs of the summing circuit are applied to daisy-chained buses 40 and 42. In order to insure that the sum outputs from each receiver board are synchronized, a pipeline structure is utilized.

Referring again to FIG. 10, the outputs of 16 processing channels (the outputs of time multiplexed delay units $22_i$) are summed four at a time by summing units 230, 232, 234 and 236. The outputs of summing units 230, 232, 234 and 236 are supplied through pipeline registers 240, 242, 244 and 246, respectively, to a four input summing unit 250. Each of the inputs to summing units 230, 232, 234 and 236 is a time multiplexed, delayed stream of data samples, as represented by the primary beam output 100 or the neighbor beam output 102 of time multiplexed delay unit $22_i$ (FIG. 4). Pipeline registers 240, 242, 244 and 246 are each clocked by the system clock. The output of summing unit 250 is supplied through a pipeline register 252 to a summing unit 254. The summing unit 254 also receives the bus input from the previous receiver board, if any. The bus input to summing unit 254 contains the summed outputs of all previous processing channels in the daisy-chain structure. The output of summing unit 254 is supplied through a series of pipeline registers 260, 262, 264 and 266 to a four-to-one multiplexer 270. The outputs of pipeline registers 262, 264 and 266 are applied to the inputs of multiplexer 270. The multiplexer 270 is controlled by the Interleave Factor signal. Registers 260, 262, 264 and 266 and multiplexer 270 permit delays of 2, 3 or 4 clock cycles to be inserted in the sum output of each receiver board, depending on the interleave factor. This permits the outputs from all the receiver boards to be synchronized for different interleave factors. Thus, the final output of the summing unit represents the time synchronized summation of the data samples for all of the processing channels. The output of the summing unit remains time multiplexed and represents the total received signal strength from focal points along one to four receive beams.

Figure 11:
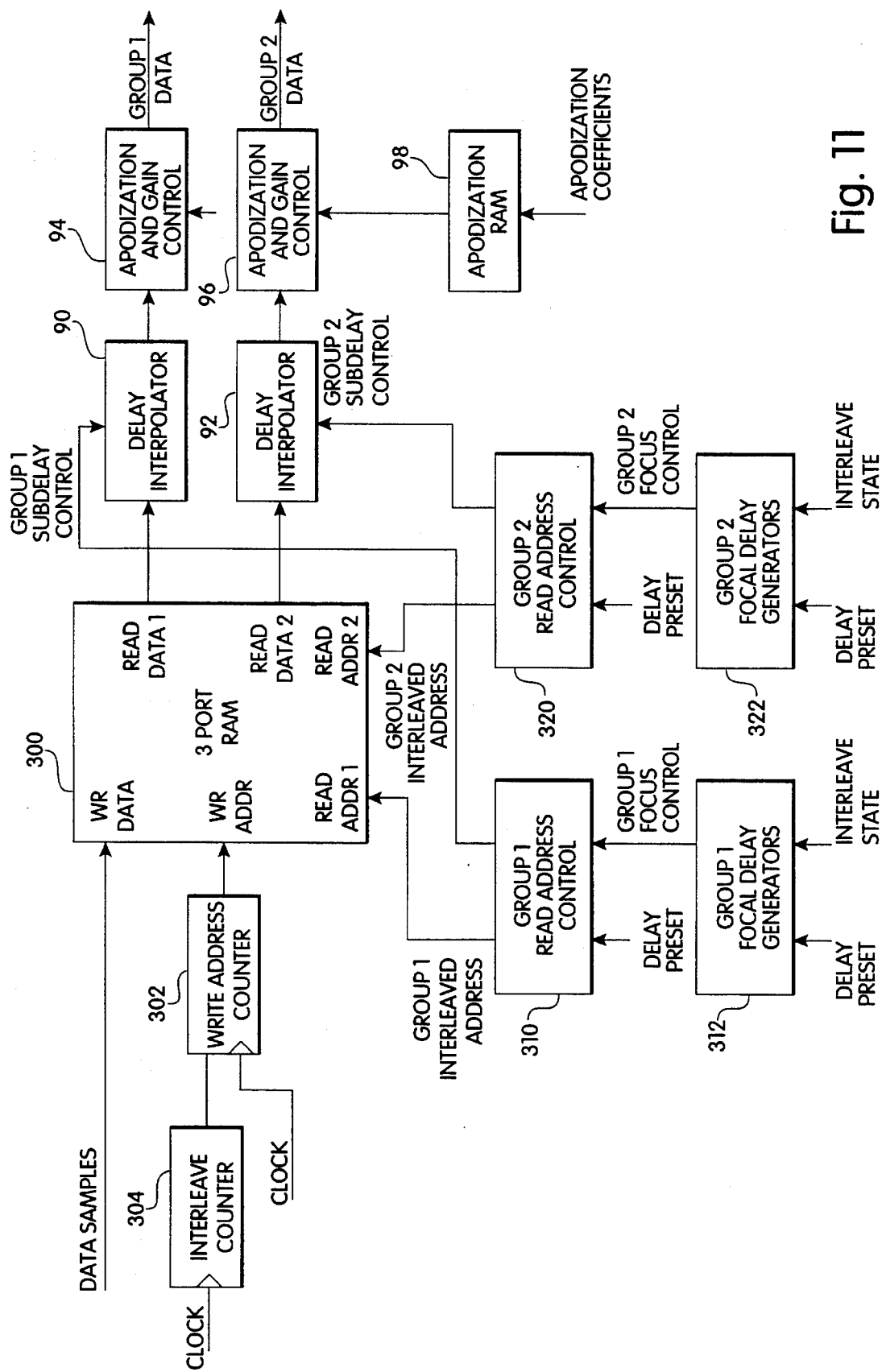
FIG. 11 is a block diagram of a second embodiment of the time multiplexed delay unit for one processing channel of the ultrasound beamformer shown in FIG. 1.

A second embodiment of the time multiplexed delay unit $22_i$ (FIG. 1) is shown in FIG. 11. Like elements in FIGS. 4 and 11 have the same reference numerals. The embodiment of FIG. 11 uses a three-port RAM 300 to generate two data streams, each representative of time multiplexed receive beams. The three-port RAM 300 has the capability of simultaneously writing data and reading data from two different addresses, with the restriction that data cannot be written and read from the same address simultaneously. Typically, the three-port RAM is implemented with two sets of sense amplifiers and decoders to permit simultaneous reading from two different addresses. The configuration of FIG. 11 produces a Group 1 data stream which may contain data samples representative of up to four receive beams and a Group 2 data stream which contains data samples representative of up to four receive beams. The Group 1 and the Group 2 beams are not required to be within a prescribed angular offset from each other as in the case of the primary and neighbor beams described above. All that is required is that each receive beam be within the pattern of transmitted ultrasound energy.

The three-port RAM 300 is addressed by a write address counter 302, which is synchronized to the system clock. An interleave counter 304 supplies a count enable signal to the write address counter. 302. The counter 304 is synchronized to the system clock and divides the system clock frequency by 1, 2, 3 or 4, depending on the desired number of receive beams (the Interleave Factor). The counters 302 and 304 correspond to the counters 114 and 116, respectively, shown in FIG. 5 and described above.

A Group 1 read address control 310 supplies a Group 1 interleaved address to the read address 1 input of three-port RAM 300. The Group 1 read address control 310 also supplies a Group 1 subdelay control to delay interpolator 90. Group 1 focal delay generators 312 supply a Group 1 focus control to Group 1 read address control 310. A Group 2 read address control 320 supplies a Group 2 interleaved address to read address 2 input of three-port RAM 300. The Group 2 read address control 320 also supplies a Group 2 subdelay control to delay interpolator 92. Group 2 focal delay generators 322 supply a Group 2 focus control signal to Group 2 read address control 320. The focal delay generators 312 and 322 have the same function and structure as the focal delay generators 82 and 88 shown in FIG. 4 and described above.

The read address controls 310 and 320 can be implemented as shown in FIG. 8 and described above, with the exception that the address counters 160, 162, 164 and 166 are not MOD 24 counters. Instead, the counters in read address controls 310 and 320 have the same number of bits as the address inputs of three-port RAM 300, plus two additional bits for subdelay control. For example, the three-port RAM may have 1024 addresses. In this case, the counters in read address controls 310 and 320 each have 12 bits: 10 bits for addressing the three-port RAM 300 and 2 bits for subdelay control.

The read data 1 output of three-port RAM 300 is supplied to delay interpolator 90 as a Group 1 data stream. The read data 2 output of three-port RAM 300 is supplied to delay interpolator 92 as a Group 2 data stream. As noted above, no relation is required between the beams in Group 1 and Group 2. The outputs of the delay interpolators 90 and 92 are supplied to apodization and gain controls 94 and 96, respectively. The delay interpolators and the apodization and gain controls correspond to those shown in FIG. 4 and described above.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f; and time multiplexed delay means responsive to delay coefficients for delaying said digital samples by time multiplexed delays to produce a stream of delayed, time multiplexed digital samples for forming two or more receive beams, said time multiplexed delay means comprising delay means for delaying said digital samples by selected delays that are quantized in increments equal to the sampling period 1/f, said delay means comprising memory means for storing said digital samples, means for writing said digital samples into said memory means, and time multiplexed read means for reading said digital samples from said memory means at locations corresponding to said time multiplexed delays, said read means comprising a read counter for each receive beam being processed, each read counter including means for addressing a location in said memory means corresponding to a desired delay, and multiplexer means for applying the output of a selected read counter to said memory means in response to an interleave control signal representative of a receive beam being processed during each clock cycle;

summing means for summing said delayed, time multiplexed digital samples to form a stream of time multiplexed output samples that is representative of said two or more receive beams; and a coefficient generator for supplying said delay coefficients to the time multiplexed delay means in each of said processing channels.

2. An ultrasound beamformer as defined in claim 1 wherein said read means further comprises means responsive to a first state of a stall command for incrementing said read counter when a constant delay is required and responsive to a second state of said stall command for stalling said read counter when a change in delay is required.

3. An ultrasound beamformer as defined in claim 2 wherein said time multiplexed delay means further comprises a focal delay generator corresponding to each read counter, each focal delay generator including means for supplying stall commands to the corresponding read counter.

4. An ultrasound beamformer as defined in claim 1 wherein said time multiplexed delay means further comprises a delay interpolator for delaying said digital samples by selected delays that are quantized in increments less than the sampling period 1/f.

5. An ultrasound beamformer as defined in claim 4 wherein said delay interpolator comprises an FIR digital filter having programmable means responsive to filter coefficients for delaying the digital samples by different delays that are quantized in increments less than the sampling period 1/f, means for supplying said filter coefficients to said FIR digital filter in response to a subdelay control signal, means for generating said subdelay control signal in response to said delay coefficients and means for storing groups of consecutive digital samples representative of each receive beam for time multiplexed application to said FIR digital filter during different clock cycles.

6. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f; and time multiplexed delay means responsive to delay coefficients for delaying said digital samples by time multiplexed delays to produce a stream of delayed, time multiplexed digital samples for forming two or more receive beams, said time multiplexed delay means comprising delay means for delaying said digital samples by selected delays that are quantized in increments equal to the sampling period 1/f, said delay means comprising memory means for storing said digital samples, means for writing said digital samples into said memory means, and time multiplexed read means for reading said digital samples from said memory means at locations corresponding to said time multiplexed delays, said means for writing said digital samples including a write address counter for addressing locations in said memory means and means for incrementing said writ address counter every 1/M clock cycles, where M represents the number of receive beams being processed;

summing means for summing said delayed, time multiplexed digital samples to form a stream of time multiplexed output samples that is representative of said two or more receive beams; and a coefficient generator for supplying said delay coefficients to the time multiplexed delay means in each of said processing channels.

7. An ultrasound beamformer as defined in claim 6 wherein said memory means comprises a two-port random access memory.

8. An ultrasound beamformer for processing received signals from an ultrasound transducer array, comprising:

a plurality of processing received signals from an ultrasound signal from an element of the transducer array and comprising:

digitizing means for converting the received signal to digital samples at a sampling rate f; and time multiplexed delay means responsive to delay coefficients for delaying said digital samples by time multiplexed delays to produce a stream of delayed, time multiplexed digital samples for forming two or more receive beams, said time multiplexed delay means comprising delay means for delaying said digital samples by selected delays that are quantized in increments equal to the sampling period 1/f, said delay means comprising memory means for storing said digital samples, means for writing said digital samples into said memory means, and time multiplexed read means for reading said digital samples from said memory means at locations corresponding to said time multiplexed delays, said time multiplexed delay means further including primary and neighbor beam delay processing means for processing said delayed digital samples to provide a first data stream containing time multiplexed digital samples for forming two or more primary beams and a second data stream containing time multiplexed digital samples for forming two or more neighbor beams, each neighbor beam having a corresponding primary beam, and each neighbor beam being within a predetermined range of angles of the corresponding primary beam;

summing means for summing said delayed, time multiplexed digital samples to form a stream of time multiplexed output samples that is representative of said two or more receive beams; and a coefficient generator for supplying said delay coefficients to the time multiplexed delay means in each of said processing channels.

9. An ultrasound beamformer as defined in claim 8 wherein said primary and neighbor beam delay processing means comprises primary beam delay means for applying a fixed additional delay to said delayed digital samples to provide said first data stream having primary beam delays, and neighbor beam delay means for removing delay increments previously applied to said delayed digital samples and applying neighbor beam delay increments to provide said second data stream.

10. An ultrasound beamformer as defined in claim 9 wherein said neighbor beam delay means comprises neighbor beam memory means for storing said delayed digital samples, time multiplexed write means for writing said delayed digital samples into said neighbor beam memory means, and time multiplexed read means for reading said delayed digital samples from said neighbor beam memory means.

11. An ultrasound beamformer as defined in claim 10 wherein said time multiplexed write means comprises a write counter corresponding to each primary beam being processed, each write counter including means for addressing a location in said neighbor beam memory means corresponding to a primary beam delay increment, and multiplexer means for applying the output of a selected write counter to said neighbor beam memory means in response to an interleave control signal representative of a receive beam being processed during each clock cycle, and wherein said time multiplexed read means comprises a read counter corresponding to each neighbor beam being processed, each read counter including means for addressing a location in said neighbor beam memory means corresponding to a neighbor beam delay increment, and multiplexer means for applying the output of a selected read counter to said neighbor beam memory means in response to said interleave control signal.

12. An ultrasound beamformer for processing received signals from an ultrasound transducer array, comprising:

a plurality of processing channels, each receiving a signal from an element of the transducer array and comprising:

digitizing means for converting the received signal to digital samples at a sampling at a sampling rate f, said digitizing means comprising an amplifier for amplifying the received signal, a limiter for limiting the amplified signal, a low pass filter for removing high frequency components from the limited signal and an analog-go-digital converter for converting the limited and filtered signal to said digital samples, said analog-to-digital converter from saturating, and said low pass filter having a cutoff frequency corresponding to the sampling rate f; and time multiplexed delay means responsive to delay coefficients for delaying said digital samples by time multiplexed delays to produce a stream of delayed, time multiplexed digital samples for forming two or more receive beams;

summing means for summing said delayed, time multiplexed digital samples to form a stream of time multiplexed output samples that is representative of said two or more receive beams; and a coefficient generator for supplying said delay coefficients to the time multiplexed delay means in each of said processing channels.

13. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f; and time multiplexed delay means responsive to delay coefficients for delaying said digital samples by time multiplexed delays to produced a stream of delayed, time multiplexed digital samples for forming two or more receive beams;

summing means for summing said delayed, time multiplexed digital samples to form a stream of time multiplexed output samples that is representative of said two or more receive beams; and a coefficient generator for supplying said delay coefficients to the time multiplexed delay means in each of said processing channels, said time multiplexed delay means, said summing means and said coefficient generator each including programmable means for processing a selectable number of receive beams.

14. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f; and time multiplexed delay means responsive to delay coefficients for delaying said digital samples by time multiplexed delays to produce a stream of delayed, time multiplexed digital samples for forming two or more receive beams;

summing means for summing said delayed, time multiplexed digital samples to form a stream of time multiplexed output samples that is representative of said two or more receive beams, aid summing means having a pipeline structure, including means for summing the delayed digital samples for a plurality of groups of channels to provide a plurality of intermediate sums during a first clock cycle and means for summing said plurality of intermediate sums during a second clock cycle to form a sum representative of said plurality of groups of channels; and a coefficient generator for supplying said delay coefficients to the time multiplexed delay means in each of said processing channels.

15. An ultrasound beamformer as defined in claim 14 wherein said summing means further includes programmable means for adding different pipeline delays to the output of said summing means in response to an interleave factor representative of the number of receive beams being processed.

16. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f; and time multiplexed delay means responsive to delay coefficients for delaying said digital samples by time multiplexed delays to produce a stream of delayed, time multiplexed digital samples for forming two or more receive beams;

summing means for summing said delayed, time multiplexed digital samples to form a stream of time multiplexed output samples that is representative of said two or more receive beams; and a coefficient generator for supplying said delay coefficients to the time multiplexed delay means in each of said processing channels, said time multiplexed delay means, said summing means and said coefficient generator being interconnected by a high speed data bus for carrying said delay coefficients and control information during transmission of ultrasound energy by said ultrasound transducer elements and for carrying said delayed digital samples when said ultrasound transducer elements are receiving ultrasound energy.

17. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f; and time multiplexed delay means responsive to delay coefficients for delaying said digital samples by time multiplexed delays to produce a stream of delayed, time multiplexed digital samples for forming two or more receive beams, said time multiplexed delay means comprising delay means for delaying said digital samples by selected delays that quantized in increments equal to the sampling period 1/f, said delay means comprising memory means for storing said digital samples, means for writing said digital samples into said memory means, and time multiplexed read means for reading said digital samples from said memory means at locations corresponding to said time multiplexed delays, said memory means comprising a three-port random access memory having a write port, a first read port and a second read port and wherein said time multiplexed read means comprises a first read address control for supplying first interleaved addresses to said first read port and a second read address control for supplying second interleaved addresses to said second read port, said first read port supplying a first stream of time multiplexed data samples in response to said first interleaved addresses and said second read port supplying a second stream of time multiplexed data samples in response to said second interleaved addresses;

summing means for summing said delayed, time multiplexed digital samples to form a stream of time multiplexed output samples that is representative of said two or more receive beams; and a coefficient generator for supplying said delay coefficient to the time multiplexed delay means in each of said processing channels.

18. An ultrasound beamformer as defined in claim 17 wherein said first and second read address controls each comprise a read counter for each receive beam being processed, each read counter including means for addressing a location in said three-port random access memory corresponding to a desired delay, and multiplexer means for applying the output of a selected read counter to said memory means in response to an interleave control signal representative of a receive beam being processed during each clock cycle.

19. An ultrasound beamformer as defined in claim 18 wherein said time multiplexed delay means further comprises a focal delay generator corresponding to each read counter, each focal delay generator including means for supplying a stall command to the corresponding read counter, a first state of the stall command incrementing said read counter when a constant delay is required and a second state of the stall command stalling said read counter when a change in delay is required.

20. An ultrasound beamformer as defined in claim 17 wherein said time multiplexed delay means further comprises delay interpolator means for delaying the digital samples in said first and second streams of time multiplexed data samples by selected delays that are quantized in increments less than the sampling period 1/f.

21. An ultrasound beamformer for processing received signals from an ultrasound transducer array, comprising:

a plurality of processing channels, each receiving a signal from an element of the transducer array and comprising:

digitizing means for converting the received signal to digital samples at a sampling rate f, said digitizing means comprising an amplifier for amplifying the received signal, a limiter for limiting the amplified signal, a low pass filter for removing high frequency components from the limited signal and an analog-to-digital converter for converting the limited and filtered signal to said digital samples, said limiter including means for preventing said analog-to-digital converter from saturating; and delay means for delaying said digital samples by selected delays to produce a stream of delayed digital samples for forming a received beam; and summing means for summing said delayed digital samples to form a stream of output samples that is representative of said receive beam.

22. An ultrasound beamformer for processing received signals form an ultrasound transducer array, comprising:

a plurality of processing channels, each receiving a signal from an element of the transducer array and comprising:

a digitizer for converting the received signal to digital samples at a sampling rate f; and a time multiplexed delay circuit responsive to delay coefficients for delaying said digital samples by time multiplexed delays to produce a stream of delayed, time multiplexed digital samples for forming two or more receive beams, said time multiplexed delay circuit comprising an integer clock delay for delaying said digital samples by selected delays that are quantized in increments equal to the sampling period 1/f, said integer clock delay comprising a memory for storing said digital samples, said time multiplexed delay circuit further comprising a circuit for writing said digital samples into said memory, and a time multiplexed read control circuit for reading said digital samples from said memory at locations corresponding to said time multiplexed delays, said read control circuit comprising a read counter for each receive beam being processed, each rad counter addressing a location in said memory corresponding to a desired delay, and a multiplexer for applying the output of a selected read counter to said memory in response to an interleave control signal representative of a receive beam being processed during each clock cycle;

a summing circuit for summing said delayed, time multiplexed digital samples to form a stream of time multiplexed output samples that is representative of said two or more receive beams; and a coefficient generator for supplying said delay coefficients to the time multiplexed delay circuit in each of said processing channels.

* * * * *